United States Patent
Boutell

(10) Patent No.: US 12,123,056 B2
(45) Date of Patent: Oct. 22, 2024

(54) SURFACE CONCATEMERIZATION OF TEMPLATES

(71) Applicant: Illumina Cambridge Limited, Saffron Walden (GB)

(72) Inventor: Jonathan Mark Boutell, Essex (GB)

(73) Assignee: ILLUMINA CAMBRIDGE LIMITED, Cambridge (GB)

( * ) Notice: Subject to any disclaimer, the term of this patent is extended or adjusted under 35 U.S.C. 154(b) by 254 days.

(21) Appl. No.: 17/153,725

(22) Filed: Jan. 20, 2021

(65) Prior Publication Data

US 2021/0155985 A1    May 27, 2021

Related U.S. Application Data

(63) Continuation of application No. 15/560,147, filed as application No. PCT/GB2016/050898 on Mar. 30, 2016, now abandoned.

(60) Provisional application No. 62/141,165, filed on Mar. 31, 2015.

(51) Int. Cl.
| | | |
|---|---|---|
| C12P 19/34 | (2006.01) | |
| C12N 15/10 | (2006.01) | |
| C12N 15/64 | (2006.01) | |
| C12Q 1/6806 | (2018.01) | |
| C12Q 1/6874 | (2018.01) | |
| C12Q 1/6853 | (2018.01) | |

(52) U.S. Cl.
CPC .......... *C12Q 1/6874* (2013.01); *C12N 15/10* (2013.01); *C12N 15/64* (2013.01); *C12Q 1/6806* (2013.01); *C12Q 1/6853* (2013.01)

(58) Field of Classification Search
USPC .......... 435/6.1, 6.11, 6.12, 91.1, 91.2, 91.51, 435/287.1, 287.2; 436/94, 501; 536/23.1, 24.3, 24.33, 25.3
See application file for complete search history.

(56) References Cited

U.S. PATENT DOCUMENTS

| | | | |
|---|---|---|---|
| 5,130,238 | A | 7/1992 | Malek et al. |
| 5,185,243 | A | 2/1993 | Ullman et al. |
| 5,455,166 | A | 10/1995 | Walker |
| 5,573,907 | A | 11/1996 | Carrino et al. |
| 5,679,524 | A | 10/1997 | Nikiforov et al. |
| 5,928,905 | A | 7/1999 | Stemmer et al. |
| 6,172,218 | B1 | 1/2001 | Brenner |

(Continued)

FOREIGN PATENT DOCUMENTS

| | | |
|---|---|---|
| EP | 0320308 | 6/1989 |
| EP | 0336731 | 10/1989 |

(Continued)

OTHER PUBLICATIONS

Bentley et al. 2008. Accurate whole human genome sequencing using reversible terminator chemistry. Nature, 456:53-59.

(Continued)

*Primary Examiner* — Frank W Lu
(74) *Attorney, Agent, or Firm* — Knobbe, Martens, Olson & Bear LLP

(57) ABSTRACT

Presented herein are methods and compositions for concatenating template strands during the bridge amplification process. The methods are useful for surface amplification at improved densities. The methods and compositions provided herein enable creation of clusters that are brighter, but at the same densities as currently achieved using standard cluster amplification.

18 Claims, 9 Drawing Sheets
Specification includes a Sequence Listing.

(56) References Cited

U.S. PATENT DOCUMENTS

| | | | |
|---|---|---|---|
| 6,210,891 | B1 | 4/2001 | Nyren et al. |
| 6,214,587 | B1 | 4/2001 | Dattagupta et al. |
| 6,258,568 | B1 | 7/2001 | Nyren |
| 6,274,320 | B1 | 8/2001 | Rothberg et al. |
| 6,306,597 | B1 | 10/2001 | Macevicz |
| 6,737,236 | B1 | 5/2004 | Pieken et al. |
| 6,969,488 | B2 | 11/2005 | Bridgham et al. |
| 7,001,792 | B2 | 2/2006 | Sauer et al. |
| 7,057,026 | B2 | 6/2006 | Barnes et al. |
| 7,115,400 | B1 | 10/2006 | Adessi et al. |
| 7,211,414 | B2 | 5/2007 | Hardin et al. |
| 7,259,258 | B2 | 8/2007 | Kozlov et al. |
| 7,315,019 | B2 | 1/2008 | Turner et al. |
| 7,329,492 | B2 | 2/2008 | Hardin et al. |
| 7,375,234 | B2 | 5/2008 | Sharpless et al. |
| 7,405,281 | B2 | 7/2008 | Xu et al. |
| 7,427,673 | B2 | 9/2008 | Balasubramanian et al. |
| 7,427,678 | B2 | 9/2008 | Pieken et al. |
| 7,582,420 | B2 | 9/2009 | Oliphant et al. |
| 7,611,869 | B2 | 11/2009 | Fan |
| 7,670,810 | B2 | 3/2010 | Gunderson et al. |
| 7,741,463 | B2 | 6/2010 | Gormley et al. |
| 7,985,565 | B2 | 7/2011 | Mayer et al. |
| 8,003,354 | B2 | 8/2011 | Shen et al. |
| 8,715,966 | B2 | 5/2014 | Xiaohai et al. |
| 2005/0100900 | A1 | 5/2005 | Kawashima et al. |
| 2006/0188901 | A1 | 8/2006 | Barnes et al. |
| 2006/0240439 | A1 | 10/2006 | Smith et al. |
| 2006/0281109 | A1 | 12/2006 | Barr Ost et al. |
| 2007/0166705 | A1 | 7/2007 | Milton et al. |
| 2008/0108082 | A1 | 5/2008 | Rank et al. |
| 2008/0280773 | A1 | 11/2008 | Fedurco et al. |
| 2009/0026082 | A1 | 1/2009 | Rothberg et al. |
| 2009/0127589 | A1 | 5/2009 | Rothberg et al. |
| 2010/0111768 | A1 | 5/2010 | Banerjee et al. |
| 2010/0137143 | A1 | 6/2010 | Rothberg et al. |
| 2010/0282617 | A1 | 11/2010 | Rothberg et al. |
| 2011/0059865 | A1 | 3/2011 | Smith et al. |
| 2012/0270305 | A1 | 10/2012 | Reed et al. |
| 2012/0316086 | A1 | 12/2012 | Lin et al. |
| 2013/0079232 | A1 | 3/2013 | Kain et al. |
| 2013/0116153 | A1 | 5/2013 | Bowen et al. |
| 2013/0260372 | A1 | 10/2013 | Buermann et al. |

FOREIGN PATENT DOCUMENTS

| | | |
|---|---|---|
| EP | 0439182 | 7/1991 |
| WO | WO 89/09835 A1 | 10/1989 |
| WO | WO 89/12696 A1 | 12/1989 |
| WO | WO 90/01069 A1 | 2/1990 |
| WO | WO 91/06678 A1 | 5/1991 |
| WO | WO 1998/44151 | 10/1998 |
| WO | WO 2004/018497 A1 | 6/2004 |
| WO | WO 2005/065814 A1 | 7/2005 |
| WO | WO 2006/064199 A1 | 6/2006 |
| WO | WO 2007/123744 A2 | 11/2007 |
| WO | WO 2010/038042 | 4/2010 |

OTHER PUBLICATIONS

"Bridge amplification" in "Illumine dye sequencing" from Wikipedia. Printed on Jul. 20, 2020.
Cockroft et al. 2008. A single-molecule nanopore device detects DNA polymerase activity with single-nucleotide resolution. J Am Chem Soc, 130:818-820.
"Concatemers" from Wikipedia. Printed on Jul. 20, 2020.
Deamer et al. 2000. Nanopores and nucleic acids: prospects for ultrarapid sequencing. Trends Biotechnol., 18:147-151.
Deamer et al. 2002. Characterization of nucleic acids by nanopore analysis. Acc. Chem. Res., 35(10):817-825.
Dean et al. 2002. Comprehensive human genome amplification using multiple displacement amplification. PNAS, 99:5261-66.
Grothues et al. 1993. PCR amplification of megabase DNA with tagged random primers (T-PCR). Nucl Acids Res, 21(5):1321-22.
Healy, K. 2007. Nanopore-based single-molecule DNA analysis. Nanomedicine, 2(4):459-481.
Korlach et al. 2008. Selective aluminum passivation for targeted immobilization of single DNA polymerase molecules in zero-mode waveguide nano structures. Proc. Natl. Acad. Sci. USA, 105:1176-1181.
Lage et al. 2003. Whole genome analysis of genetic alterations in small DNA samples using hyperbranched strand displacement amplification and array-CGH. Genome Res, 13:294-307.
Levene et al. 2003. Zero-mode waveguides for single-molecule analysis at high concentrations. Science, 299:682-686.
Li et al. 2003. DNA molecules and configurations in a solid-state nanopore microscope. Nat. Mater., 2:611-615.
Lizardi et al. 1998. Mutation detection and single-molecule counting using isothermal rolling-circle amplification. Nat Genet, 19:225-232.
Lundquist et al. 2008. Parallel confocal detection of single molecules in real time. Opt. Lett., 33(9):1026-1028.
Metzker. 2005. Emerging technologies in DNA sequencing. Genome Research, 15:1767-1776.
"Polymerase chain reaction" from Wikipedia, the free encyclopedia. Printed on Nov. 9, 2019.
Ronaghi et al. 1996. Real-time DNA sequencing using detection of pyrophosphate release. Anal Biochem, 242(1):84-89.
Ronaghi et al. 1998. A sequencing method based on real-time pyrophosphate. Science, 281(5375):363.
Ronaghi et al. 2001. Pyrosequencing sheds light on DNA sequencing. Genome Res, 11(1):3-11.
Ruparel et al. 2005. Design and synthesis of a 3'-O-allyl photocleavable fluorescent nucleotide as a reversible terminator for DNA sequencing by synthesis. Proc Natl Acad Sci USA, 102(17): 5932-5937.
Soni et al. 2007. Progress toward ultrafast DNA sequencing using solid-state nanopores. Clin. Chem., 53(11):1996-2001.
Walker et al. 1992. Strand displacement amplification—an isothermal, in vitro DNA amplification technique. Nucl Acids Res, 20:1691-96.
Walker et al. 1995. Molecular Methods for Virus Detections, Academic Press, Inc. pp. 329-349.
Written Opinion and International Search Report of the International Searching Authority mailed Jul. 18, 2016 for International Application No. PCT/GB2016/050898 filed Mar. 30, 2016.

SEQUENCE LISTING

<160> NUMBER OF SEQ ID NOS: 8

<210> SEQ ID NO 1
<211> LENGTH: 20
<212> TYPE: DNA
<213> ORGANISM: Artificial sequence
<220> FEATURE:
<223> OTHER INFORMATION: P5 region sequence

<400> SEQUENCE: 1
aatgatacgg cgaccaccga                                                    20

<210> SEQ ID NO 2
<211> LENGTH: 21
<212> TYPE: DNA
<213> ORGANISM: Artificial sequence
<220> FEATURE:
<223> OTHER INFORMATION: P7 region sequence

<400> SEQUENCE: 2
caagcagaag acggcatacg a                                                  21

<210> SEQ ID NO 3
<211> LENGTH: 20
<212> TYPE: DNA
<213> ORGANISM: Artificial sequence
<220> FEATURE:
<223> OTHER INFORMATION: anti-P5 sequence

<400> SEQUENCE: 3
tcggtggtcg ccgtatcatt                                                    20

<210> SEQ ID NO 4
<211> LENGTH: 21
<212> TYPE: DNA
<213> ORGANISM: Artificial sequence
<220> FEATURE:
<223> OTHER INFORMATION: anti-P7 sequence

<400> SEQUENCE: 4
tcgtatgccg tcttctgctt g                                                  21

<210> SEQ ID NO 5
<211> LENGTH: 29
<212> TYPE: DNA
<213> ORGANISM: Artificial sequence
<220> FEATURE:
<223> OTHER INFORMATION: amplification primer P5 sequence

<400> SEQUENCE: 5
aatgatacgg cgaccaccga gauctacac                                          29

<210> SEQ ID NO 6
<211> LENGTH: 24
<212> TYPE: DNA
<213> ORGANISM: Artificial sequence
<220> FEATURE:
<223> OTHER INFORMATION: amplification primer P7 sequence
<220> FEATURE:
<221> NAME/KEY: misc_feature
<222> LOCATION: 22
<223> OTHER INFORMATION: n is 8-oxo-g

<400> SEQUENCE: 6
caagcagaag acggcatacg anat                                               24

```
<210> SEQ ID NO 7
<211> LENGTH: 29
<212> TYPE: RNA
<213> ORGANISM: Artificial sequence
<220> FEATURE:
<223> OTHER INFORMATION: capture primer P5 sequence

<400> SEQUENCE: 7
gtgtagatct cggtggtcgc cgtatcatt                                29

<210> SEQ ID NO 8
<211> LENGTH: 24
<212> TYPE: RNA
<213> ORGANISM: Artificial sequence
<220> FEATURE:
<223> OTHER INFORMATION: capture primer P7 sequence

<400> SEQUENCE: 8
atctcgtatg ccgtcttctg cttg                                     24
```

SURFACE CONCATEMERIZATION OF TEMPLATES

CROSS REFERENCE TO RELATED APPLICATIONS

This application is a continuation of U.S. patent application Ser. No. 15/560,147, filed on Sep. 20, 2017, now abandoned which is the U.S. National Phase of PCT/GB2016/050898 filed Mar. 30, 2016 and published in English as WO 2016/156845 on Oct. 6, 2016, which claims the benefit of U.S. Provisional Application No. 62/141,165, filed Mar. 31, 2015, the disclosures of which are incorporated herein by reference in their entireties.

REFERENCE TO SEQUENCE LISTING

The present application is being filed along with a sequence listing in electronic format. The sequence listing is provided as a file entitled SeqListing_ILLINC.402C1.txt, created Jan. 20, 2021, which is 1.86 KB in size. The information in the electronic format of the sequence listing is incorporated herein by reference in its entirety.

BACKGROUND

The task of cataloguing human genetic variation and correlating this variation with susceptibility to disease is daunting and expensive. A drastic reduction in this cost is imperative for advancing the understanding of health and disease. A reduction in sequencing costs will require a number of technical advances in the field. Technical advances that could reduce the cost of genome analysis include: (1) library generation; (2) highly-parallel clonal amplification and analysis; (3) development of robust cycle sequencing biochemistry; (4) development of ultrafast imaging technology; and (5) development of algorithms for sequence assembly from short reads.

The creation of clonal amplifications in a highly-parallel manner is important for cost-effective sequencing. Sequencing is generally performed on clonal populations of DNA molecules traditionally prepared from plasmids grown from picking individual bacterial colonies. In the human genome project, each clone was individually picked, grown-up, and the DNA extracted or amplified out of the clone. In recent years, there have been a number of innovations to enable highly-parallelized analysis of DNA clones particularly using array-based approaches. In the simplest approach, the library can be analyzed at the single molecule level, which by its very nature is clonal. The major advantage of single molecule sequencing is that cyclic sequencing can occur asynchronously since each molecule is read out individually. In contrast, analysis of clonal amplifications requires near quantitative completion of each sequencing cycle, otherwise background noise progressively grows with each ensuing cycle severely limiting read length. As such, clonal analysis places a bigger burden on the robustness of the sequencing biochemistry and may potentially limit read lengths.

Thus, there exists a need to develop methods to improve genomics analysis and provide more cost effective methods for sequence analysis. The present invention satisfies this need and provides related advantages as well.

BRIEF SUMMARY

The methods and compositions provided herein enable surface amplification at improved densities. Described herein are methods for concatenating template strands during the bridge amplification process, such that each flowcell surface primer can end up with a multiple copies of the template strand extended onto it. The methods and compositions provided herein enable creation of clusters that are brighter, but at the same densities as currently achieved using standard cluster amplification. Brighter clusters may have a number of advantages, for example, better quality of reads, support for longer read lengths, faster scan times for sequencing, and increased system robustness.

Presented herein is a method of preparing immobilized templates for a nucleic acid sequencing reaction comprising: (a) providing a solid support having a forward and reverse amplification primer immobilized thereon; (b) providing a target nucleic acid, wherein the target nucleic acid comprises: (i) a first region of known sequence complementary to the forward amplification primer; (ii) a first template region; (iii) a second region of known sequence substantially identical to the reverse amplification primer, wherein the first template region is between the first region of known sequence and the second region of known sequence; and (iv) a third region of known sequence complementary to the forward amplification primer, wherein the first template region and the second region of known sequence are between the first region of known sequence and the third region of known sequence; (c) applying the target nucleic acid to the solid support under conditions suitable for hybridization whereby the first region of known sequence hybridizes to the forward amplification primer; and (d) extending the hybridized forward amplification primer to generate an immobilized template comprising a complementary copy of the target nucleic acid.

In some embodiments, the method can further comprise: (e) denaturing the target nucleic acid from the immobilized template; (f) hybridizing the immobilized template to the reverse amplification primer, whereby a complementary copy of the second flanking sequence hybridizes to the reverse amplification primer; and (g) extending the hybridized reverse amplification primer to generate a second immobilized strand comprising the first template region positioned between the first region of known sequence and the second region of known sequence.

In some embodiments, the method can further comprise: (h) denaturing the second immobilized strand from the first immobilized template; (i) hybridizing the second immobilized strand to the first immobilized template, whereby the first region of known sequence of the second immobilized strand hybridizes to a complementary copy of the first region of known sequence in the immobilized template; (j) extending a 3' OH of the first region of known sequence to generate a concatemer of the second immobilized strand; and (k) extending a 3' OH of the complementary copy of the first region of known sequence to generate a concatemer of the first immobilized template.

In some embodiments, the method can further comprise: (l) denaturing the concatemers and repeating steps (i), (j) and (k) to generate further concatemers of each strand.

In some aspects of the above embodiments, the forward amplification primer can comprise a forward complementarity region, said forward complementarity region having complementarity to a reverse complementarity region of the reverse amplification primer.

In some aspects, the first complementarity region is positioned directly 5' of a region having complementarity to the first region of known sequence of the target nucleic acid.

In some aspects, the reverse complementarity region is positioned directly 5' of a region having sequence substantially identical to the second region of known sequence of the target nucleic acid.

In some aspects, the forward complementarity region and second complementarity region are configured such that repeated cycles of hybridization and extension produces a concatemer of the first immobilized strand, each copy in the concatemer separated from the next by sequence from the forward complementarity region.

In some aspects, the forward complementarity region and second complementarity region are configured such that repeated cycles of hybridization and extension produces a concatemer of the second immobilized strand, each copy in the concatemer separated from the next by sequence from the reverse complementarity region.

In some aspects, the concatemers comprises multiple copies of said target nucleic acid molecule of at least 10, 20, 50, 100, 200, 500, 1000, 2000, 3000, 4000, 5000, 6000, 7000, 8000, 9000 or at least 10,000 copies.

In some aspects, the solid support is planar. In some aspects, the solid support comprises microwells.

In some aspects, the target nucleic acid has a length of at least 10, 20, 50, 100, 200 or at least 500 nucleotides.

In some aspects, the target nucleic acid further comprises a fourth region of known sequence substantially identical to the reverse amplification primer, wherein the first region of known sequence, the first template region and the second region of known sequence are between the third region of known sequence and the fourth region of known sequence.

In some aspects, the forward amplification primer comprises a non-nucleotide chemical linker moiety positioned to prevent copying of any nucleotides that are 5' of the non-nucleotide chemical linker moiety. In some aspects, the reverse amplification primer comprises a non-nucleotide chemical linker moiety positioned to prevent copying of any nucleotides that are 5' of the non-nucleotide chemical linker moiety. In aspects of any of the above-described embodiments, the non-nucleotide chemical linker moiety can comprises a diol moiety. In some aspects, the non-nucleotide chemical linker moiety comprises a non-nucleotide linker tethering the primer to the solid support.

In some embodiments, the method can further comprise sequencing the target nucleic acid. For example, in some aspects, sequencing the target nucleic acid comprises: hybridizing one or more sequencing primers to the first immobilized template or the second immobilized strand; extending the sequencing primers by incorporating one or more labeled nucleotides into the nascent strand; and detecting the labeled nucleotides, thereby obtaining sequence information about the target nucleic acid.

In some embodiments, the target nucleic acid is prepared by amplifying with a pair of primers configured with a binding moiety whereby one strand of an amplification product generated using the pair of primers can be separated from the opposite strand. In some aspects, the binding moiety comprises biotin and can be separated by binding to a solid support comprising streptavidin.

The details of one or more embodiments are set forth in the accompanying drawings and the description below. Other features, objects, and advantages will be apparent from the description and drawings, and from the claims.

DETAILED DESCRIPTION

Standard technology for surface amplification of nucleic acid templates ("clustering") has enabled very high densities (500-600 k/mm$^2$) on a typical flowcell. However, there remains a need for improved methodologies for surface amplification of nucleic acid templates. The methods and compositions provided herein enable surface amplification at improved densities. Described herein are methods for concatenating template strands during the bridge amplification process, such that each flowcell surface primer can end up with a multiple copies of the template strand extended onto it. The methods and compositions provided herein enable creation of clusters that are brighter, but at the same densities as currently achieved using standard cluster amplification. Brighter clusters may have a number of advantages, for example, better quality of reads, support for longer read lengths, faster scan times for sequencing, and increased system robustness.

Figure 1:
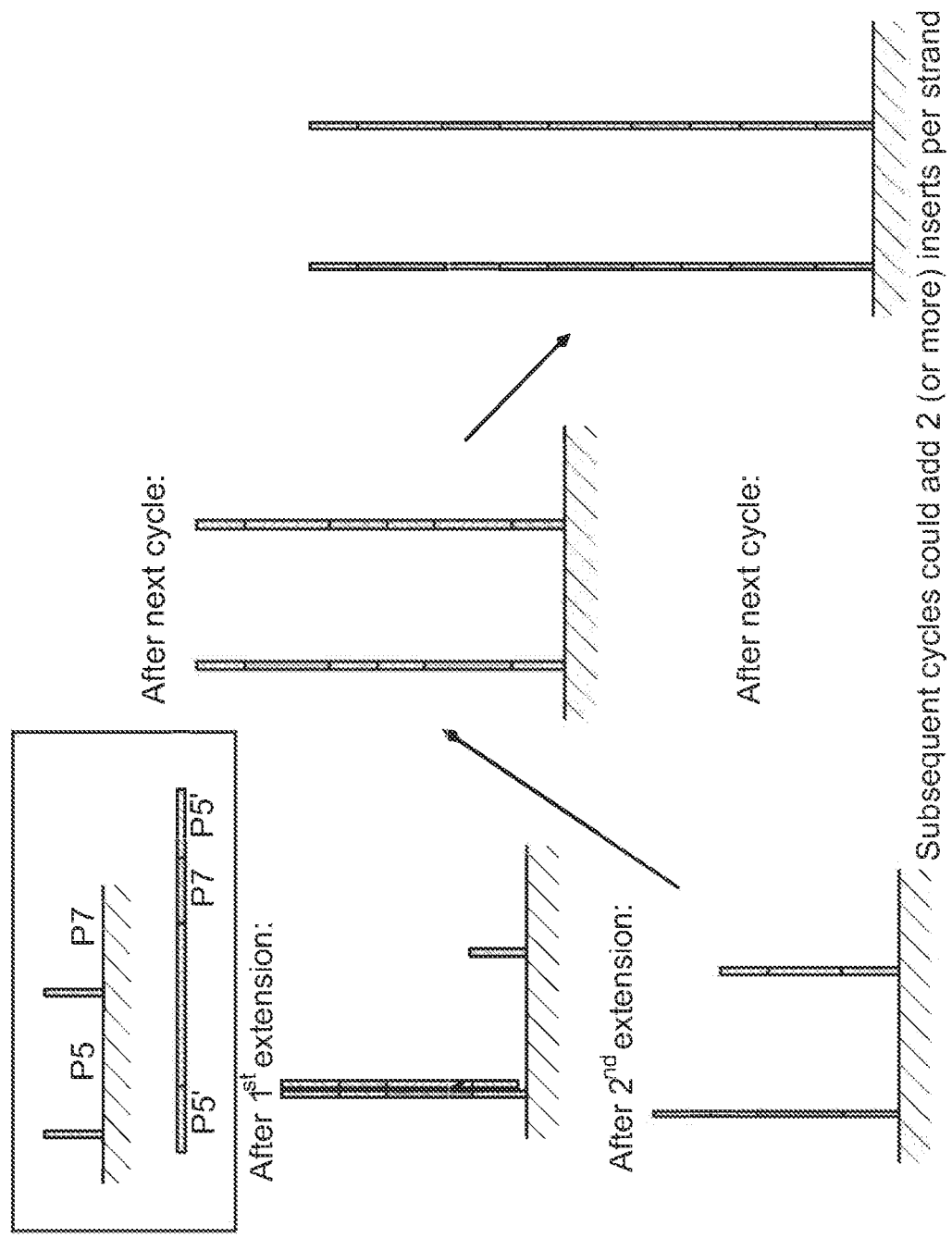
FIG. 1 is a schematic showing solid phase amplification according to one embodiment.

One embodiment is illustrated in FIG. 1, which sets forth a method of forming concatemers of a target nucleic acid. As shown in the boxed portion of FIG. 1, a solid support is provided having immobilized thereon a plurality of forward and reverse amplification primers, designated P5 and P7 in the figure. A target nucleic acid is also provided, having a first region of known sequence (P5'), complementary to P5 primer, a second region of known sequence substantially identical to the reverse amplification primer (P7) and a third region of known sequence (P5'), complementary to P5 primer. A first template region is positioned between the first (P5') and second (P7) regions of known sequence. The target nucleic acid is applied to the solid support under conditions suitable for hybridization such that the P5' sequence hybridizes to the P5 sequence of the immobilized primer. The primer is extended under conditions favorable to extension, for example in the presence of a DNA polymerase and dNTPs. The resulting extension product is an immobilized template comprising a complementary copy of the target nucleic acid, as illustrated in FIG. 1 after the first extension.

Further rounds of bridge amplification can include denaturing the target nucleic acid from the immobilized template and allowing the immobilized template to hybridize to the reverse amplification primer. In the example shown in FIG. 1, the complementary copy of the second known sequence (P7') hybridizes to the reverse primer (P7) and is extended under extension conditions described above. The resulting extension product is a second immobilized strand comprising the first template region positioned between the first region of known sequence and the second region of known sequence, as illustrated in FIG. 1 after the second extension. Subsequent cycles of denaturation, hybridization and extension allow the process to continue such that the second immobilized strand can hybridize to the first immobilized template and one or both 3' OH of the second immobilized strand and/or the first immobilized template are extended to generate further extension products. The further extension products that result from these additional cycles are concatemers of one or both of the second immobilized strand and/or the first immobilized template, as illustrated in FIG. 1 after the next cycles. The concatemers can include 2 or more copies of the template region (or complement thereof) positioned in between the known sequences. In some embodiments, the concatemers can include 2, 3, 4, 5, 6, 7, 8, 9, 10, 20, 50, 100, 200, 500, 1000, 2000, 3000, 4000, 5000, 6000, 7000, 8000, 9000 or more than 10,000 copies of the template region (or complement thereof) positioned in between the known sequences. After rounds of amplification, a sequencing primer in solution can be hybridized to a region of known sequence and extended. The sequencing primer will hybridize to multiple locations on the same immobilized strand and/or immobilized template. Multiple sequencing reactions can therefore take place on the same strand, resulting in a signal that is greatly amplified over previous methods, where only one signal per strand is generated.

As used herein, the term "concatemer" refer to a long continuous nucleic acid molecule that contains multiple copies of the same sequences linked in series. The multiple copies may be separated by other sequence, for example, by known sequence that flanks the concatemerized sequence on the 3' and/or the 5' end. Any number of copies of flanking sequence may be interspersed between the concatemerized sequence. In some embodiments, the concatemers can include 2, 3, 4, 5, 6, 7, 8, 9, 10, 20, 50, 100, 200, 500, 1000, 2000, 3000, 4000, 5000, 6000, 7000, 8000, 9000 or more than 10,000 copies of a template region (or complement thereof) on a single concatemer. In some embodiments, the concatemers can comprise 2, 3, 4, 5, 6, 7, 8, 9, 10, 20, 50, 100, 200, 500, 1000, 2000, 3000, 4000, 5000, 6000, 7000, 8000, 9000 or more than 10,000 copies of known sequence, positioned in a repeating manner between copies of the known sequences. Further exemplification of this embodiment is set forth in Example 1 below.

Figure 2:
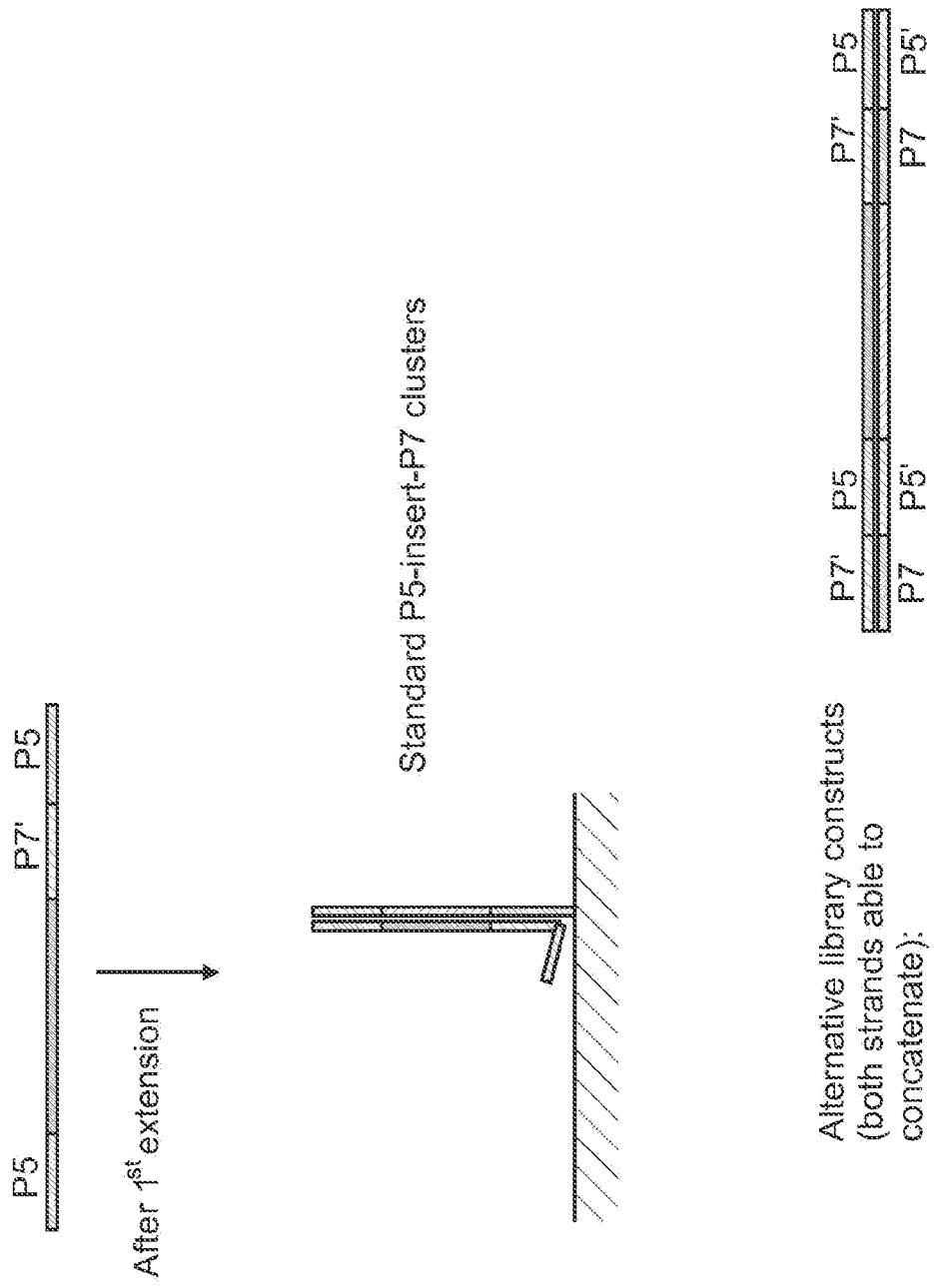
FIG. 2 is a schematic showing alternative library constructs for use in solid phase amplification.

FIG. 2 illustrates an alternate embodiment, where a strand complementary to the target nucleic acid is provided. This may naturally result in embodiments where the target nucleic acid is provided in double-stranded form. As shown in FIG. 2, the opposite strand hybridizes to the reverse amplification primer and is extended. However, in contrast to the embodiment illustrated in FIG. 1, a single copy of the target nucleic acid is generated. Further cycles of amplification will not generate concatemers, as shown in FIG. 2. To avoid this result, alternative library constructs can be generated that comprise both the first and second known regions on both the 3' end and the 5' end of the double-stranded construct, as illustrated in FIG. 2. Amplification of either the top strand or the bottom strand will generate concatemers, in a manner similar to that shown in FIG. 1.

Figure 3:
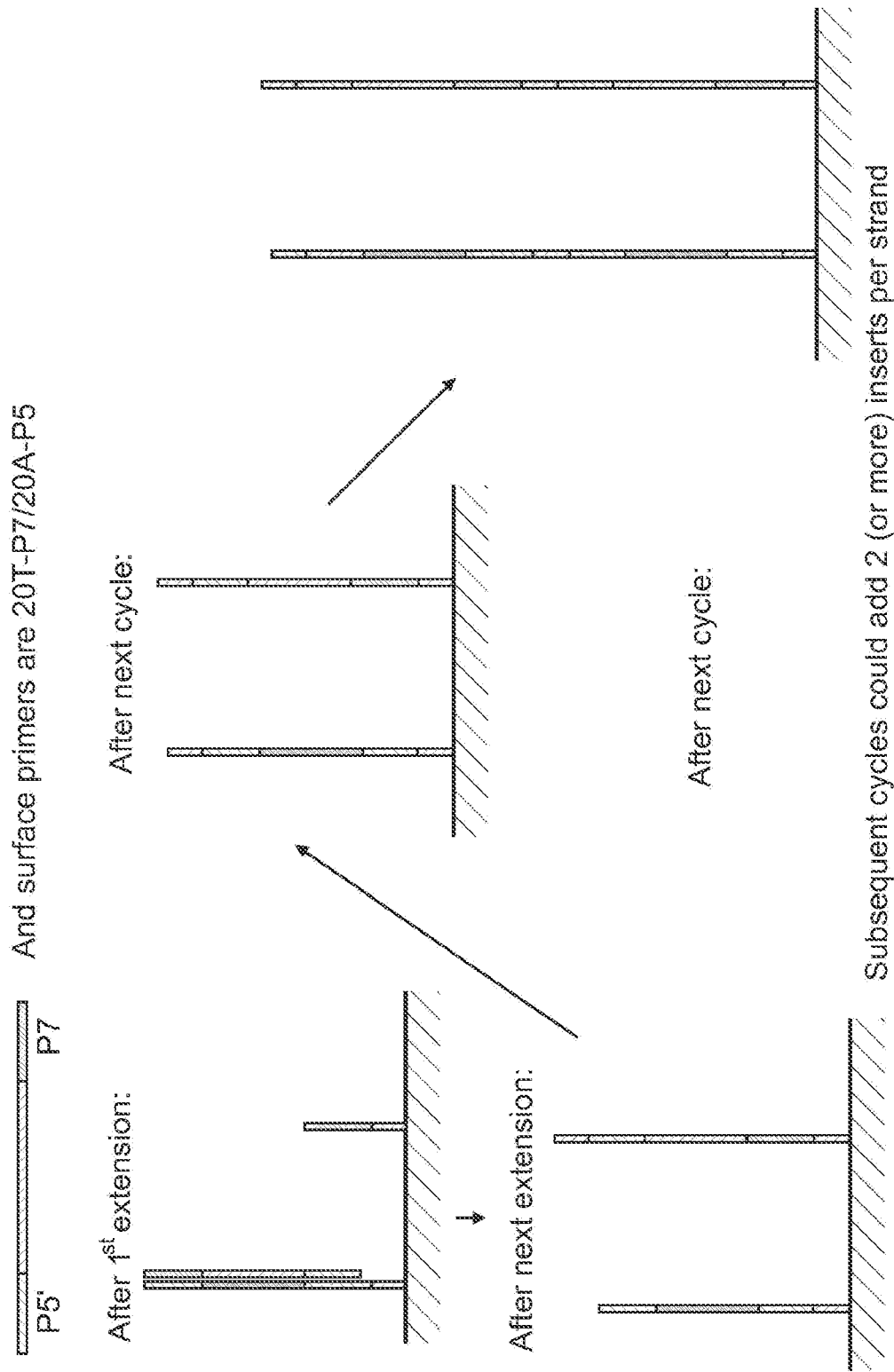
FIG. 3 is a schematic showing solid phase amplification according to one embodiment.

FIG. 3 illustrates another embodiment, wherein the forward and reverse amplification primers comprise additional sequence positioned 5' of the sequence that hybridizes to the known sequence. In some embodiments, the additional sequence of the forward primer is complementary to the additional sequence of the reverse primer. For example, as illustrated in FIG. 3, the surface primers comprise an oligo dA and oligo dT sequence positioned 5' of the P5 and P7 sequences (designated 20T-P7 and 20A-P5). Thus, after a first extension cycle, the immobilized template comprises the complementarity sequence (20mer A) immobilized at the 5' end of the template, as shown in FIG. 1 after the first extension. After a subsequent extension, the resulting copy comprises the complement of the complementarity sequence (20mer T) immobilized at the 5' end of the copied strand and again at the 3' end of the extension product. As further rounds of amplification take place, the complementarity sequences are incorporated in tandem, flanking the known sequences, for example P5 and P7, as illustrated in FIG. 3. Further exemplification of this embodiment is set forth in Example 2 below.

Cluster Amplification

Described herein are methods for concatenating template strands during the bridge amplification process. Bridge amplification is also referred herein as "cluster amplification." In some embodiments, the immobilized DNA fragments are amplified using cluster amplification methodologies as exemplified by the disclosures of U.S. Pat. Nos. 7,985,565 and 7,115,400, the contents of each of which is incorporated herein by reference in its entirety. The incorporated materials of U.S. Pat. Nos. 7,985,565 and 7,115,400 describe methods of solid-phase nucleic acid amplification, which allow amplification products to be immobilized on a solid support in order to form arrays comprised of clusters or "colonies" of immobilized nucleic acid molecules. Each cluster or colony on such an array is formed from a plurality of identical immobilized polynucleotide strands and a plurality of identical immobilized complementary polynucleotide strands. The arrays so-formed are generally referred to herein as "clustered arrays". The products of solid-phase amplification reactions such as those described in U.S. Pat. Nos. 7,985,565 and 7,115,400 are so-called "bridged" structures formed by annealing of pairs of immobilized polynucleotide strands and immobilized complementary strands, both strands being immobilized on the solid support at the 5' end, preferably via a covalent attachment. Cluster amplification methodologies are examples of methods wherein an immobilized nucleic acid template is used to produce immobilized amplicons. Other suitable methodologies can also be used to produce immobilized amplicons from immobilized DNA fragments produced according to the methods provided herein. For example one or more clusters or colonies can be formed via solid-phase PCR whether one or both primers of each pair of amplification primers are immobilized.

In other embodiments, the immobilized DNA fragments are amplified in solution. For example, in some embodiments, the immobilized DNA fragments are cleaved or otherwise liberated from the solid support and amplification primers are then hybridized in solution to the liberated molecules. In other embodiments, amplification primers are hybridized to the immobilized DNA fragments for one or more initial amplification steps, followed by subsequent amplification steps in solution. Thus, in some embodiments an immobilized nucleic acid template can be used to produce solution-phase amplicons.

It will be appreciated that any of the amplification methodologies described herein or generally known in the art can be utilized with universal or target-specific primers to amplify immobilized DNA fragments. Suitable methods for amplification include, but are not limited to, the polymerase chain reaction (PCR), strand displacement amplification (SDA), transcription mediated amplification (TMA) and nucleic acid sequence based amplification (NASBA), as described in U.S. Pat. No. 8,003,354, which is incorporated herein by reference in its entirety. The above amplification methods can be employed to amplify one or more nucleic acids of interest. For example, PCR, including multiplex PCR, SDA, TMA, NASBA and the like can be utilized to amplify immobilized DNA fragments. In some embodiments, primers directed specifically to the nucleic acid of interest are included in the amplification reaction.

Other suitable methods for amplification of nucleic acids can include oligonucleotide extension and ligation, rolling circle amplification (RCA) (Lizardi et al., Nat. Genet. 19:225-232 (1998), which is incorporated herein by reference) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835, all of which are incorporated by reference) technologies. It will be appreciated that these amplification methodologies can be designed to amplify immobilized DNA fragments. For example, in some embodiments, the amplification method can include ligation probe amplification or oligonucleotide ligation assay (OLA) reactions that contain primers directed specifically to the nucleic acid of interest. In some embodiments, the amplification method can include a primer extension-ligation reaction that contains primers directed specifically to the nucleic acid of interest. As a non-limiting example of primer extension and ligation primers that can be specifically designed to amplify a nucleic acid of interest, the amplification can include primers used for the GoldenGate assay (Illumina, Inc., San Diego, CA) as exemplified by U.S. Pat. Nos. 7,582,420 and 7,611,869, each of which is incorporated herein by reference in its entirety.

Exemplary isothermal amplification methods that can be used in a method of the present disclosure include, but are not limited to, Multiple Displacement Amplification (MDA) as exemplified by, for example Dean et al., Proc. Natl. Acad. Sci. USA 99:5261-66 (2002) or isothermal strand displacement nucleic acid amplification exemplified by, for example U.S. Pat. No. 6,214,587, each of which is incorporated herein by reference in its entirety. Other non-PCR-based methods that can be used in the present disclosure include, for example, strand displacement amplification (SDA) which is described in, for example Walker et al., Molecular Methods for Virus Detection, Academic Press, Inc., 1995; U.S. Pat. Nos. 5,455,166, and 5,130,238, and Walker et al., Nucl. Acids Res. 20:1691-96 (1992) or hyperbranched strand displacement amplification which is described in, for example Lage et al., Genome Research 13:294-307 (2003), each of which is incorporated herein by reference in its entirety. Isothermal amplification methods can be used with the strand-displacing Phi 29 polymerase or Bst DNA polymerase large fragment, 5'→3' exo- for random primer amplification of genomic DNA. The use of these polymerases takes advantage of their high processivity and strand displacing activity. High processivity allows the polymerases to produce fragments that are 10-20 kb in length. As set forth above, smaller fragments can be produced under isothermal conditions using polymerases having low processivity and strand-displacing activity such as Klenow polymerase.

Additional description of amplification reactions, conditions and components are set forth in detail in the disclosure of U.S. Pat. No. 7,670,810, which is incorporated herein by reference in its entirety.

Another nucleic acid amplification method that is useful in the present disclosure is Tagged PCR which uses a population of two-domain primers having a constant 5' region followed by a random 3' region as described, for example, in Grothues et al. Nucleic Acids Res. 21(5):1321-2 (1993), incorporated herein by reference in its entirety. The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers can be removed and further replication can take place using primers complementary to the constant 5' region.

Sequencing Methods

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminscent signals that are produced due to incorporation of a nucleotides at the features of the array. An image can be obtained after the array is treated with a particular nucleotide type (e.g. A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026, the disclosures of which are incorporated herein by reference. This approach is being commercialized by Solexa (now Illumina Inc.), and is also described in WO 91/06678 and WO 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments, some or all of the nucleotide monomers can include reversible terminators. In such embodiments, reversible terminators/cleavable fluors can include fluor linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199, PCT Publication No. WO 07/010,251, U.S. Patent Application Publication No. 2012/0270305 and U.S. Patent Application Publication No. 2013/0260372, the disclosures of which are incorporated herein by reference in their entireties.

Some embodiments can utilize detection of four different nucleotides using fewer than four different labels. For example, SBS can be performed utilizing methods and systems described in the incorporated materials of U.S. Patent Application Publication No. 2013/0079232. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Patent Application Publication No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as $\alpha$-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and $\gamma$-phosphate-labeled nucleotides as described, for example, in U.S. Pat. Nos. 7,329,492 and 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. No. 7,405,281 and U.S. Patent Application Publication No. 2008/0108082 (each of which is incorporated herein by reference). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, C T, a Life Technologies subsidiary) or sequencing methods and systems described in US 2009/0026082 A1; US 2009/0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

An advantage of the methods set forth herein is that they provide for rapid and efficient detection of a plurality of target nucleic acid in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in US 2010/0111768 A1 and U.S. Ser. No. 13/273,666, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, CA) and devices described in U.S. Ser. No. 13/273,666, which is incorporated herein by reference.

In the methods and compositions presented herein, polynucleotides are immobilized to the solid support. In some embodiments, the polynucleotides are covalently immobilized to the support. When referring to immobilization of molecules (e.g. nucleic acids) to a solid support, the terms "immobilized" and "attached" are used interchangeably herein and both terms are intended to encompass direct or indirect, covalent or non-covalent attachment, unless indicated otherwise, either explicitly or by context. In certain embodiments of the invention covalent attachment may be preferred, but generally all that is required is that the molecules (e.g. nucleic acids) remain immobilized or attached to the support under the conditions in which it is intended to use the support, for example in applications requiring nucleic acid amplification and/or sequencing.

Certain embodiments of the invention may make use of solid supports comprised of an inert substrate or matrix (e.g. glass slides, polymer beads etc.) which has been functionalized, for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass, particularly polyacrylamide hydrogels as described in WO 2005/065814 and US 2008/0280773, the contents of which are incorporated herein in their entirety by reference. In such embodiments, the biomolecules (e.g. polynucleotides) may be directly covalently attached to the intermediate material (e.g. the hydrogel) but the intermediate material may itself be non-covalently attached to the substrate or matrix (e.g. the glass substrate). The term "covalent attachment to a solid support" is to be interpreted accordingly as encompassing this type of arrangement.

Exemplary covalent linkages include, for example, those that result from the use of click chemistry techniques. Exemplary non-covalent linkages include, but are not limited to, non-specific interactions (e.g. hydrogen bonding, ionic bonding, van der Waals interactions etc.) or specific interactions (e.g. affinity interactions, receptor-ligand interactions, antibody-epitope interactions, avidin-biotin interactions, streptavidin-biotin interactions, lectin-carbohydrate interactions, etc.). Exemplary linkages are set forth in U.S. Pat. Nos. 6,737,236; 7,259,258; 7,375,234 and 7,427,678; and US Pat. Pub. No. 2011/0059865 A1, each of which is incorporated herein by reference.

The terms "target nucleic acid," "target nucleic acid molecule," "target nucleic acid species" and any grammatical equivalent thereof, refer to nucleic acid molecules that are desired to be detected, sequenced or otherwise analyzed. Any of a variety of desired target nucleic acid molecules can be utilized, including but not limited to exons, or nucleic acid molecules complementary thereto; cDNA molecules, or nucleic acid molecules complementary thereto; untranslated regions (UTRs) or nucleic acids complementary thereto; promoter and/or enhancer regions, or nucleic acid molecules complementary thereto; evolutionary conserved regions (ECRs), or nucleic acid molecules complementary thereto; transcribed genomic regions, or nucleic acid molecules complementary thereto. Any of a variety of methods can be used to obtain targeted nucleic acid molecules, as disclosed herein. Such methods include, but are not limited to, obtaining a targeted nucleic acid molecule using hybridization-extension capture enrichment; using targeted restriction sites, for example, using an oligonucleotide engineered with a hairpin having a Type IIS restriction enzyme site such as a FokI restriction enzyme site and a locus-specific region; using locus-specific hyperbranched rolling circle amplification; using random-locus-specific primer amplification; using multiplex emulsion PCR; using multiplex bridge PCR; using padlock probe amplification; and using mini-libraries from targeted libraries, as disclosed herein.

As used herein, the terms "target nucleic acid sequence," "sample nucleic acid sequence" and like terms refer to nucleic acid sequences obtained from samples that are desired to be analyzed.

A nucleic acid sample that is amplified, sequenced or otherwise manipulated in a method disclosed herein can be, for example, DNA or RNA. Exemplary DNA species include, but are not limited to, genomic DNA (gDNA), mitochondrial DNA, chloroplast DNA, episomal DNA, viral DNA and copy DNA (cDNA). One non-limiting example of a subset of genomic DNA is one particular chromosome or one region of a particular chromosome. Exemplary RNA species include, without limitation, coding RNA such as messenger RNA (mRNA), and non-coding RNA (ncRNA) such as transfer RNA (tRNA), microRNA (miRNA), small nuclear RNA (snRNA) and ribosomal RNA (rRNA). Further species of DNA or RNA include fragments or portions of the species listed above or amplified products derived from these species, fragments thereof or portions thereof. The methods described herein are applicable to the above species encompassing all or part of the complement present in a cell. For example, using methods described herein the sequence of a substantially complete genome can be determined or the sequence of a substantially complete targeted nucleic acid sequences such as mRNA or cDNA complement of a cell can be determined.

Target DNA molecules of different sequence may be prepared by mixing a number, greater than one, of individual DNA molecules. In the preferred procedure, genomic DNA is fragmented into small molecules, preferably less than 1000 base pairs in length. Fragmentation of DNA may be achieved by a number of methods including: enzymatic digestion, chemical cleavage, sonication, nebulisation, or hydroshearing, preferably nebulization.

Known sequences may be added to the 3' and 5' ends of target nucleic acid sequences using any of a number of methodologies known in the art, as exemplified, for example by those set forth in U.S. Pat. Nos. 7,741,463, 7,985,565, and 7,115,400, each of which is incorporated by reference herein in its entirety. For example, in some embodiments, known sequences are added by ligating adapters to nucleic acid fragments. In some embodiments, known sequences are added by amplification using primers having additional known sequence at their 5' ends. In some embodiments, known sequences can comprise sequences that are identical or complimentary to amplification primers immobilized on a solid support. For example, in certain embodiments, known sequence can include either one of two universal capture regions, such as P5 or P7 regions. A P5 region includes the nucleotide sequence 5'-AATGATACGGCGAC-CACCGA-3' (SEQ ID NO: 1). A P7 region includes the nucleotide sequence 5'-CAAGCAGAAGACGGCAT-ACGA-3' (SEQ ID NO: 2). In certain embodiments, the known sequence is the reverse complement of the P5 region sequence ("anti-P5": 5'-TCGGTGGTCGCCGTATCATT-3' (SEQ ID NO: 3)) or the P7 region sequence ("anti-P7": 5'-TCGTATGCCGTCTTCTGCTTG-3' (SEQ ID NO: 4)) amplification primer. In certain embodiments, the oligonucleotide can hybridize with Illumina® amplification primers P5 (paired end) (5'-AATGATACGGCGAC-CACCGAGAUCTACAC-3' (SEQ ID NO: 5)) or P7 (paired end) (5'-CAAGCAGAAGACGGCATACGA(8-oxo-G)AT-3' (SEQ ID NO: 6)). In certain embodiments, the oligonucleotide can hybridize with the reverse complement of the Illumina® capture primer P5 (paired end) ("anti-P5 (paired end)": 5'-GTGTAGATCTCGGTGGTCGCCGTATCATT-3' (SEQ ID NO: 7)) or P7 (paired end) ("anti-P7 (paired end)": 5'-ATCTCGTATGCCGTCTTCTGCTTG-3' (SEQ ID NO: 8)).

The terms "solid surface," "solid support" and other grammatical equivalents herein refer to any material that is appropriate for or can be modified to be appropriate for the attachment of the transposome complexes. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, ceramics, resins, silica or silica-based materials including silicon and modified silicon, carbon, metals, inorganic glasses, plastics, optical fiber bundles, and a variety of other polymers. Particularly useful solid supports and solid surfaces for some embodiments are located within a flow cell apparatus. Exemplary flow cells are set forth in further detail below.

In some embodiments, the solid support comprises a patterned surface suitable for immobilization of transposome complexes in an ordered pattern. A "patterned surface" refers to an arrangement of different regions in or on an exposed layer of a solid support. For example, one or more of the regions can be features where one or more transposome complexes are present. The features can be separated by interstitial regions where transposome complexes are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. In some embodiments, the transposome complexes are randomly distributed upon the solid support. In some embodiments, the transposome complexes are distributed on a patterned surface. Exemplary patterned surfaces that can be used in the methods and compositions set forth herein are described in U.S. Ser. No. 13/661,524 or US Pat. App. Publ. No. 2012/0316086 A1, each of which is incorporated herein by reference.

In some embodiments, the solid support comprises an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The composition and geometry of the solid support can vary with its use. In some embodiments, the solid support is a planar structure such as a slide, chip, microchip and/or array. As such, the surface of a substrate can be in the form of a planar layer. In some embodiments, the solid support comprises one or more surfaces of a flowcell. The term "flowcell" as used herein refers to a chamber comprising a solid surface across which one or more fluid reagents can be flowed. Examples of flowcells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

In some embodiments, the solid support or its surface is non-planar, such as the inner or outer surface of a tube or vessel. In some embodiments, the solid support comprises microspheres or beads. By "microspheres" or "beads" or "particles" or grammatical equivalents herein is meant small discrete particles. Suitable bead compositions include, but are not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon, as well as any other materials outlined herein for solid supports may all be used. "Microsphere Detection Guide" from Bangs Laboratories, Fishers Ind. is a helpful guide. In certain embodiments, the microspheres are magnetic microspheres or beads.

The beads need not be spherical; irregular particles may be used. Alternatively or additionally, the beads may be porous. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller or larger beads may be used.

EXAMPLE 1

This example describes solid phase amplification according to one embodiment, as illustrated in FIG. 1. A standard universal PhiX or CT418 library containing P5 and P7' regions was used to attach the additional P5' at the 5' end of the already prepared library. This was accomplished by performing additional 18 PCR cycles. The libraries were diluted to 200 pM final and amplified using either standard primer or P7-P5' primer. Each 50 ul PCR reaction contained 22 µl of H2O, 25 µl of 2× Phusion Mastermix (NEB), 1 µl each of the appropriate primer and DNA. After PCR, the resulting library concentrations were determined by the Nanodrop (Thermo Scientific) and diluted to 10 nM in buffer EB (QIAGEN)+0.05% Tween20. A flowcell was prepared by grafting HEG primers (lanes 1-4) or standard PE primers (lanes 5-8) using the protocol described in U.S. Pat. Nos. 8,536,477, 8,715,966, and U.S. Patent Application Pub. 2008/0280773, the content of each of which is incorporated by reference herein in its entirety. The libraries generated above were used to generate clusters on the grafted flowcell.

Figure 4A:
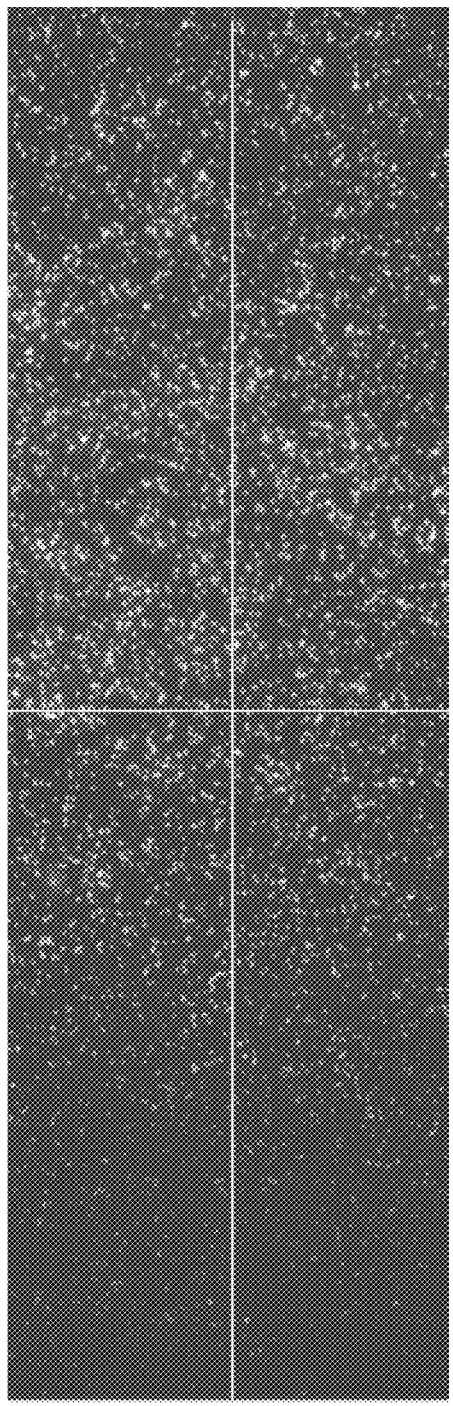
FIG. 4A is a fluorescence microscope image of amplification clusters according standard protocols compared to one embodiment presented herein.
Figure 4A:
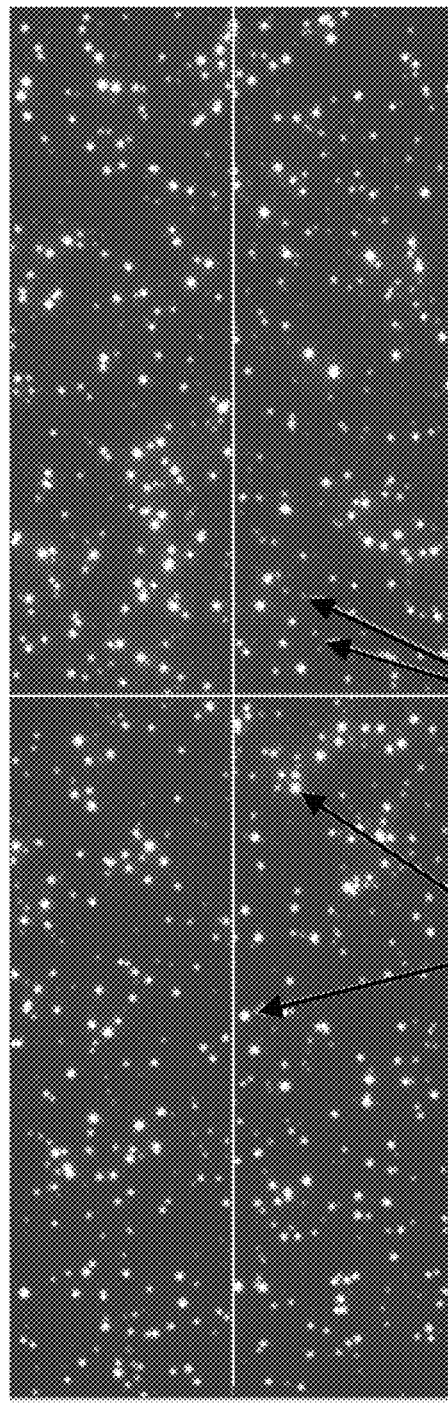
Figure 4B:
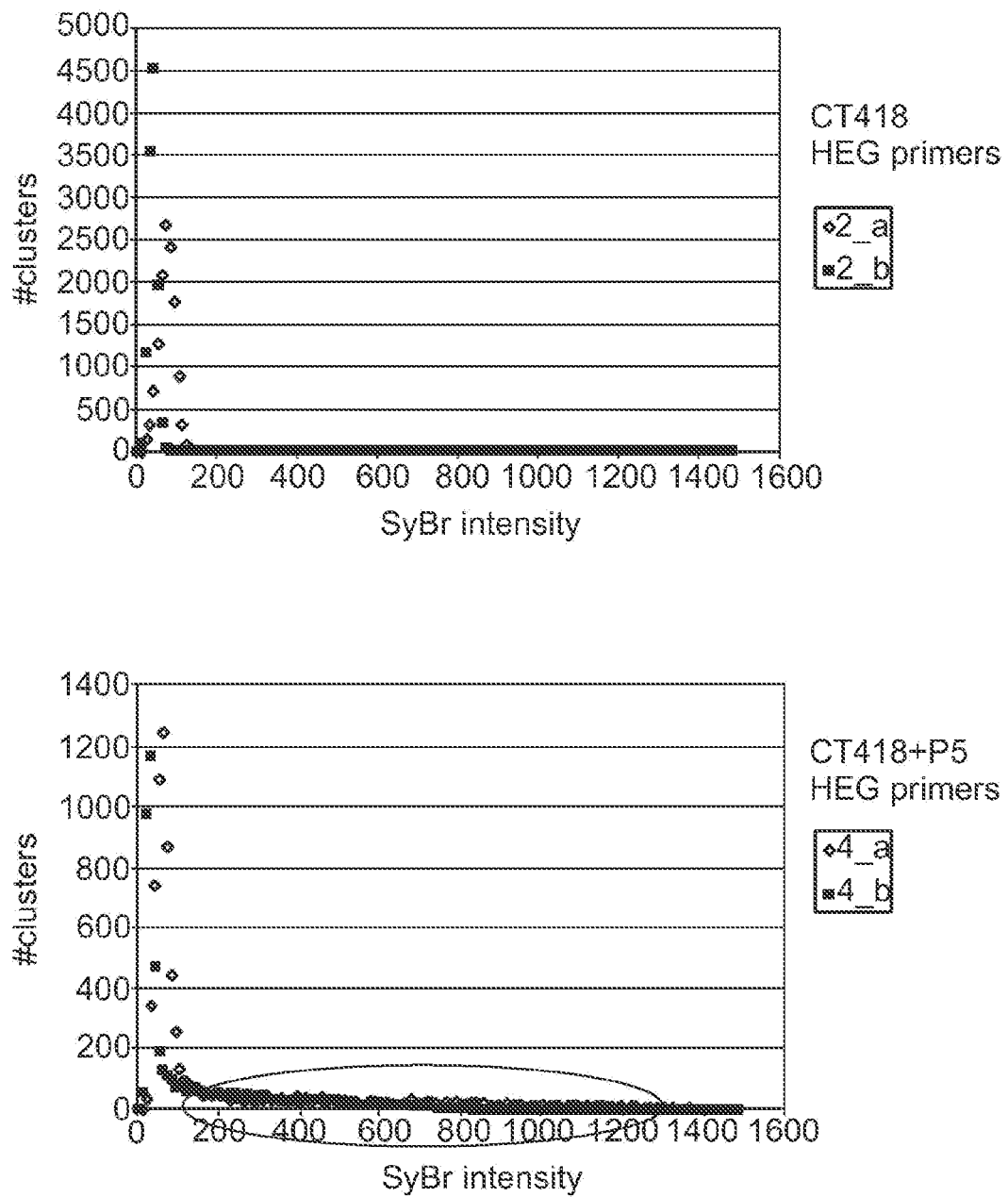
FIG. 4B is a plot of number of clusters versus the SYBR signal intensity from the flowcells described in FIG. 4A.

The clusters were amplified using TruSeq cluster generation kit for Genome Analyzer (Illumina) as per manufacturer's recommended protocol for 35 cycles. The flow cell was stained with SYBR Green (Molecular Probes) and imaged on a fluorescence microscope. As shown in the top panel of FIG. 4A, the clusters generated with standard primers resulted in normal clusters whereas the same with extra P5 modified primers were shown to result in a mix of large and normal clusters (FIG. 4A bottom panel). The plots of number of clusters versus the SYBR signal intensity from the flowcells described in FIG. 4A are shown in FIG. 4B. The clusters from standard primers resulted in low SYBR intensity (top graph) whereas those from modified primer with added P5 resulted in 10 times higher intensity (bottom graph).

Figure 5:
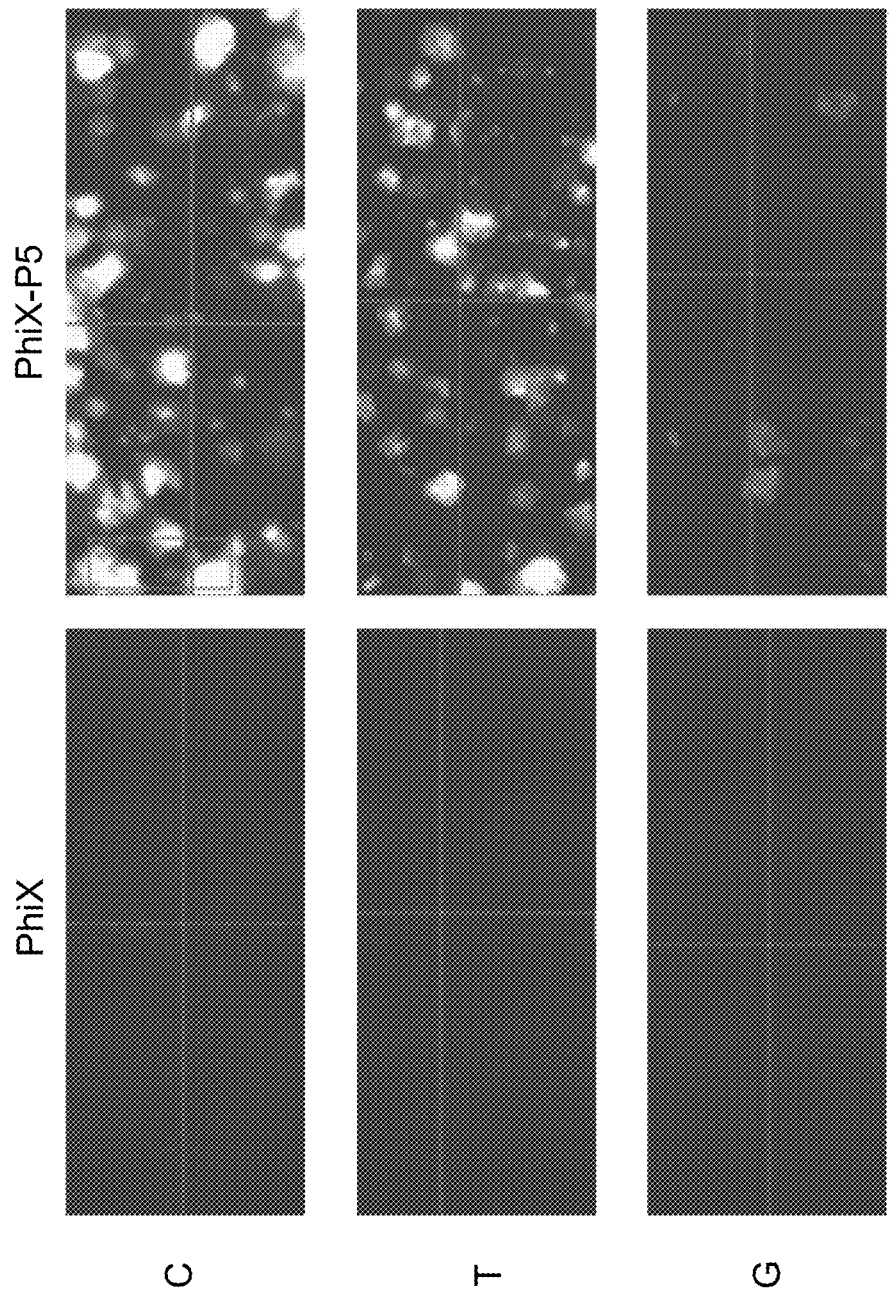
FIG. 5 is a set of fluorescence images of fluorescent nucleotides C, T and G incorporated into clusters amplified according to standard protocols or according to one embodiment presented herein.

The flowcell was then prepared to do a first cycle of sequencing incorporation, using a white light fluorophore set. The first cycle images of C, T and G with the grayscale of the image adjusted to the brightness of the T image on the modified primer lane showed that the clusters using the modified primers are brighter than the clusters made on standard primers. (FIG. 5)

EXAMPLE 2

Figure 6:
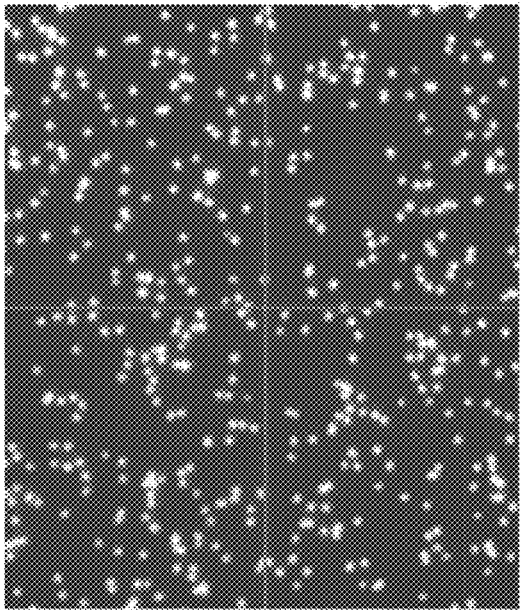
FIG. 6 shows fluorescence images (top) and histograms (bottom) of clusters amplified according to standard protocols or according to one embodiment presented herein.
Figure 6:
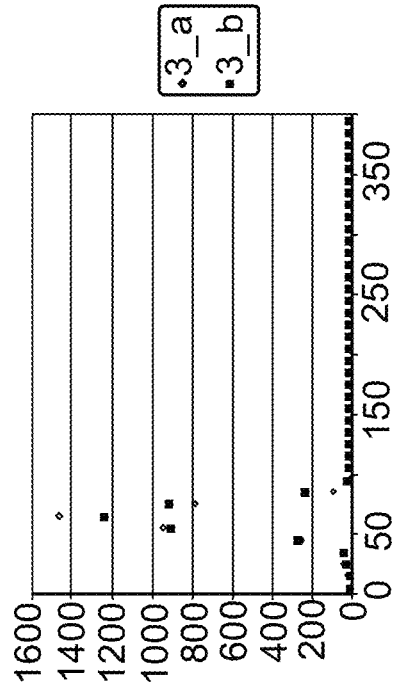
Figure 6:
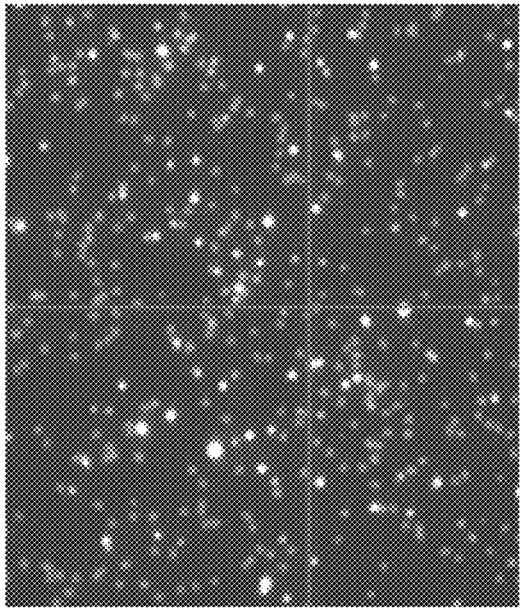
Figure 6:
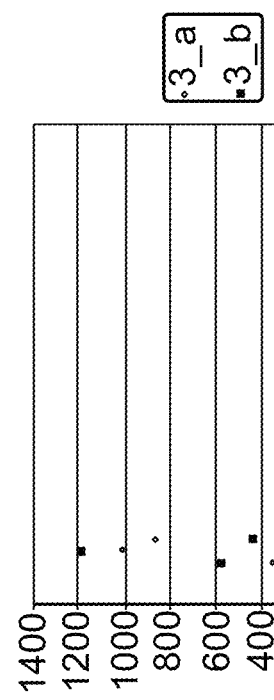

This example describes solid phase amplification according to an embodiment, as illustrated in FIG. 3. The experiments reported in FIG. 6 show the results from concatemerization of 20T/A linkers on the P5/P7 grafting primers (referred as 20T-P7/20A-P5) instead of attaching the concatemer facilitating primers on to the library during PCR process. In this experiment, the flowcell was grafted with 20A/T Paired-end P5/P7 primers alongside standard primers. The standard grafting protocol as described in incorporated materials of U.S. Pat. Nos. 8,536,477, 8,715,966, and U.S. Patent Application Pub. 2008/0280773 was followed and this grafted flowcell was used for cluster amplification on a cBOT clonal amplification system (Illumina Cat #SY-301-2002) using the TruSeq cluster generation kit for Genome Analyzer (Illumina) as per manufacturer's recommended protocol. CT418 libraries were used as template; amplified 105 cycles at 60° C. The flowcell was stained with SYBR Green and imaged as described in FIG. 4. The plots of number of clusters versus SYBR signal intensity showed that using 20T-P7/20A-P5 surface primers (6A) the cluster brightness increased compared to the standard surface primers (6B). However, fewer clusters with higher intensity were observed as compared to the example given in FIGS. 4 and 5.

Figure 7:
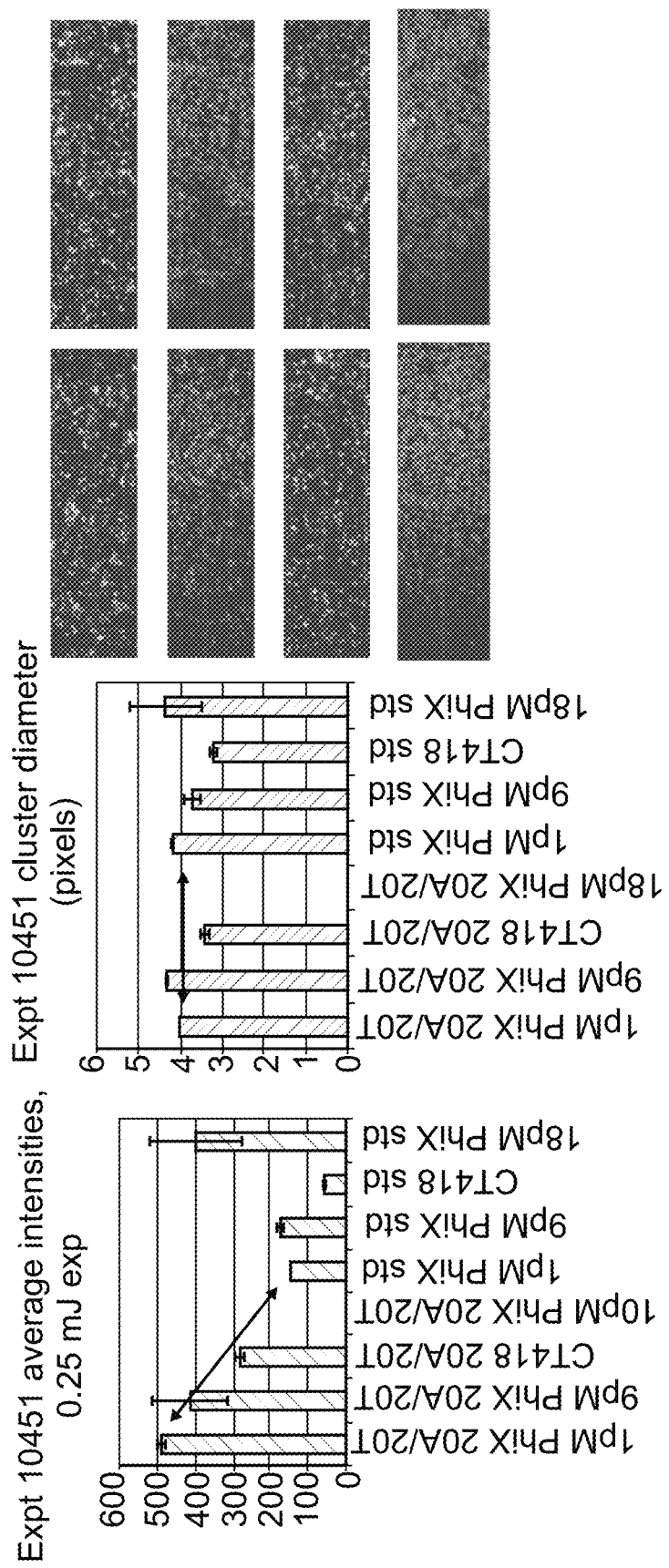
FIG. 7 shows a comparison of cluster intensity and size for various amplification protocols.

Effect of Temperature on Cluster intensity: Temperature ranges from 50° to 60° C. and amplification cycles ranging from 25 to 45 were tested for cluster generation. The grafting of flowcell and the experiment procedure were as described above for FIG. 6 except temperatures of 50 and 55° C. were tested for the cluster amplification for 35 or 45 cycles. As shown in FIG. 7, the 20T/20A surface primers amplified at 50° C. and stained with SYBR Green showed that 20T/20A clusters are 3-5 times brighter than those with standard surface primers (7A). The cluster diameter remained the same for 20T/20A surface primers and standard primers (7B). The libraries used were 1, 9 and 18 pM PhiX and 1 pM CT418. The inventors found that at temperatures at or below 55° C. and 45-cycle amplification resulted in brighter clusters using 20T/20A primers compared to standard primers. Increasing the Bst polymerase concentration along with increased extension times to 72 sec from standard 36 sec used during bridge amplification also resulted in brighter clusters when 20T/20A primers were used compared to standard clusters (data not shown).

Figure 8:
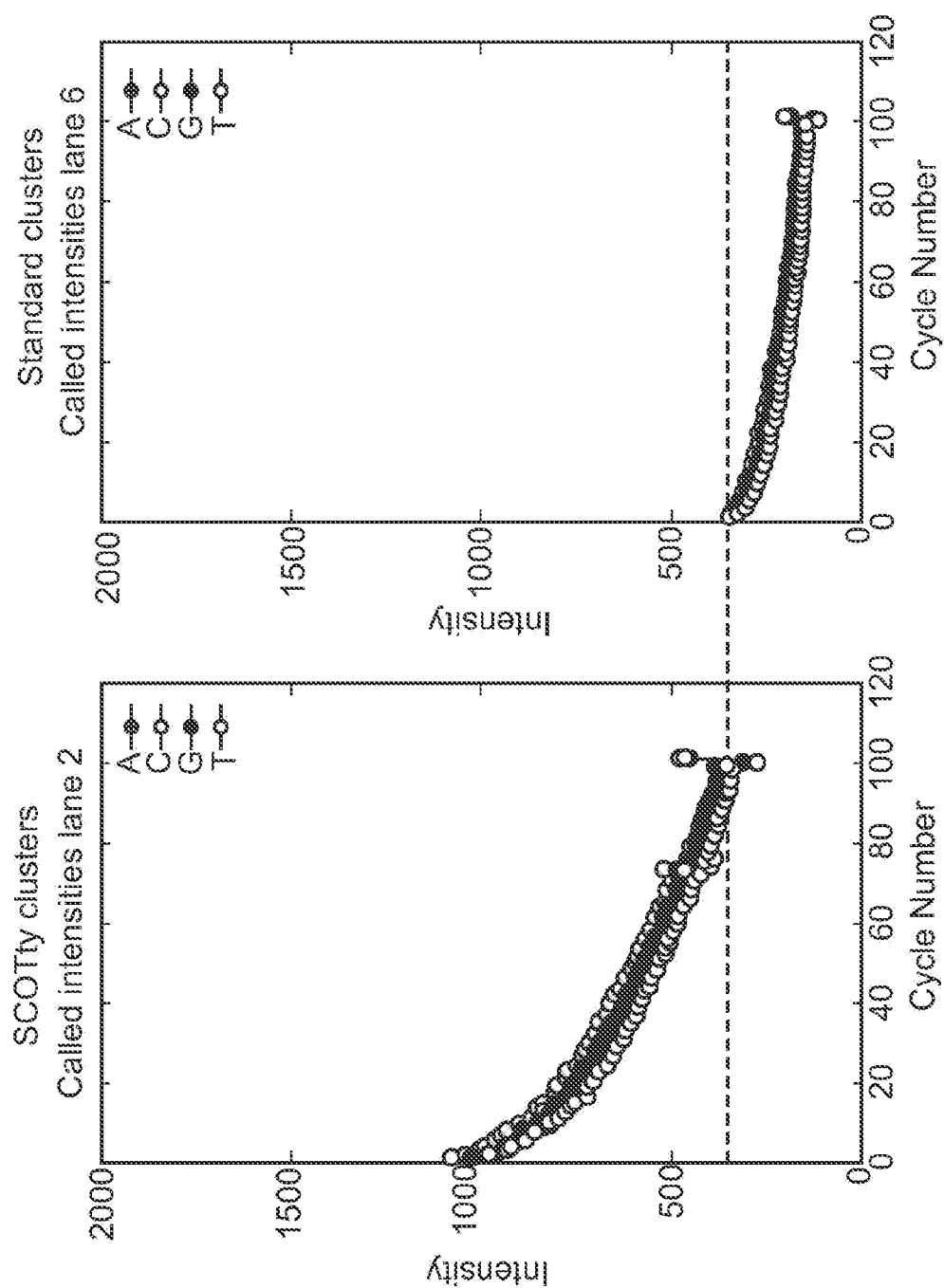
FIG. 8 shows a comparison of signal intensity over 100 cycles in surface concatemer-containing clusters versus standard clusters.

FIG. 8 is a side-by-side comparison of cluster intensity over cycle number during a standard 100 cycle sequencing run on a GA, showing that the intensity of 20T-P7/20A-P5 primer clusters at the end of a 100 cycle run is similar to the intensity of clusters with standard primers at the start of the run.

Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

What is claimed is:

1. A method of preparing a concatemer of a first immobilized template and a concatemer of a second immobilized template during a bridge amplification reaction comprising:
   (a) providing a solid support having a forward amplification primer and a reverse amplification primer immobilized thereon, wherein the forward amplification primer and the reverse amplification primer are immobilized to the solid support by their 5' ends and adjacent to each other on the solid support;
   (b) providing a single-stranded target nucleic acid, wherein the target nucleic acid comprises:
      (i) a first region of known sequence complementary to the forward amplification primer;
      (ii) a first template region;
      (iii) a second region of known sequence identical to the reverse amplification primer, wherein the first template region is located between the first region of known sequence and the second region of known sequence; and
      (iv) a third region of known sequence complementary to the forward amplification primer, wherein the first template region and the second region of known sequence are located between the first region of known sequence and the third region of known sequence;
   (c) applying the target nucleic acid to the solid support under conditions suitable for hybridization whereby the first region of known sequence of the target nucleic acid hybridizes to the forward amplification primer and produces a hybridized forward amplification primer;
   (d) generating a first immobilized template comprising a complementary strand of the target nucleic acid by extending the hybridized forward amplification primer and producing a first hybridization complex formed by the target nucleic acid and the first immobilized template;
   (e) denaturing the target nucleic acid from the first immobilized template of the first hybridization complex;
   (f) producing a hybridized reverse amplification primer by hybridizing the first immobilized template to the reverse amplification primer, whereby a complementary strand of the second region of known sequence of the first immobilized template hybridizes to the reverse amplification primer; and
   (g) generating a second immobilized template comprising the first template region positioned between the first region of known sequence and the second region of known sequence by extending the hybridized reverse amplification primer and producing a second hybridization complex formed by the first immobilized template and the second immobilized template;
   (h) denaturing the second immobilized template from the first immobilized template of the second hybridization complex;
   (i) producing an annealing complex by reannealing the second immobilized template to the first immobilized template, whereby the first region of known sequence of the second immobilized template hybridizes to a complementary strand of the first region of known sequence in the first immobilized template;
   (j) generating the concatemer of the second immobilized template by extending a 3' OH of the first region of known sequence of the second immobilized template of the annealing complex; and
   (k) generating the concatemer of the first immobilized template by extending a 3' OH of the complementary strand of the first region of known of the first immobilized template sequence of the annealing complex.

2. The method of claim 1, further comprising:
   (l) generating a hybridized concatemer complex formed by the concatemer of the first immobilized template and the concatemer of the second immobilized template;
   (m) denaturing the hybridized concatemer complex;
   (n) producing an annealing concatemer complex by reannealing the concatemer of the first immobilized template and the concatemer of the second immobilized template;
   (o) generating a different concatemer of the second immobilized strand by extending a 3' OH of the first region of known sequence of the second immobilized template of the annealing concatemer complex;
   (p) generating a different concatemer of the first immobilized template by extending a 3' OH of the complementary strand of the first region of known of the first immobilized template of the annealing concatemer complex;
   (q) generating a different hybridized concatemer complex formed by the different concatemer of the first immobilized template and the different concatemer of the second immobilized template;

(r) denaturing the different hybridized concatemer complex formed by the different concatemer of the first immobilized template and the different concatemer of the second immobilized template;

(s) producing a different annealing concatemer complex by reannealing the different concatemer of the first immobilized template and the different concatemer of the second immobilized template;

(t) generating a different concatemer of the second immobilized strand by extending a 3' OH of the first region of known sequence of the second immobilized template of the different annealing concatemer complex; and (u) generating a different concatemer of the first immobilized template by extending a 3' OH of the complementary strand of the first region of known of the first immobilized template of the different annealing concatemer complex.

3. The method of claim 2, wherein, after repeating steps (q) to (u) for multiple times, the different concatemer of the second immobilized template comprises at least 10, 20, 50, 100, 200, 500, 1000, 2000, 3000, 4000, 5000, 6000, 7000, 8000, 9000 or 10,000 copies of the target nucleic acid.

4. The method of claim 3, wherein the different concatemer of the first immobilized template comprises multiple copies of the complementary strand of the target nucleic acid and one copy of the complementary strand of the target nucleic acid in the different concatemer of the first immobilized template is separated from other copies of the complementary strand of the target nucleic acid by the forward complementarity region of the forward amplification primer.

5. The method of claim 1, wherein the forward amplification primer comprises a forward complementarity region, said forward complementarity region having complementarity to a reverse complementarity region of the reverse amplification primer.

6. The method of claim 5, wherein the forward complementarity region is positioned directly on 5' of a region of the forward amplification primer having complementarity to the first region of known sequence of the target nucleic acid.

7. The method of claim 5, wherein the reverse complementarity region is positioned directly on 5' of a region of the reverse amplification primer having sequence substantially identical to the second region of known sequence of the target nucleic acid.

8. The method of claim 5, wherein the different concatemer of the second immobilized template comprises multiple copies of the target nucleic acid and each copy of the target nucleic acid in the different concatemer of the second immobilized template is separated by the reverse complementarity region of the reverse amplification primer.

9. The method of claim 1, wherein said solid support is planar.

10. The method of claim 1, wherein said solid support comprises microwells.

11. The method of claim 1, wherein said target nucleic acid has a length of at least 10, 20, 50, 100, 200 or 500 nucleotides.

12. The method of claim 1, wherein said target nucleic acid further comprises a fourth region of known sequence substantially identical to the reverse amplification primer, wherein the first region of known sequence, the first template region and the second region of known sequence are located between the third region of known sequence and the fourth region of known sequence.

13. The method of claim 1, wherein either of the forward amplification primer and the reverse amplification primer comprises a non-nucleotide chemical linker moiety to prevent amplifying any nucleotide located on 5' of the non-nucleotide chemical linker moiety.

14. The method of claim 13, wherein the non-nucleotide chemical linker moiety comprises a diol.

15. The method of claim 13, wherein the non-nucleotide chemical linker moiety comprises a non-nucleotide linker tethering the forward amplification primer or the reverse amplification primer to the solid support.

16. The method of claim 1, further comprising sequencing the target nucleic acid.

17. The method of claim 16, wherein said sequencing the target nucleic acid comprises:
hybridizing one or more sequencing primers to the first immobilized template or the second immobilized template;
producing a nascent strand by extending the hybridized sequencing primers and incorporating one or more labeled nucleotides into the hybridized sequencing primers; and
detecting the labeled nucleotides on the nascent strand, thereby obtaining a sequence information of the target nucleic acid.

18. The method of claim 1, further comprises producing an amplification product by amplifying a nucleic acid with a pair of primers comprising a binding moiety and preparing the target nucleic acid by separating its opposite strand from the amplification product.

* * * * *